United States Patent [19]

Cordes et al.

[11] Patent Number: 5,011,985
[45] Date of Patent: Apr. 30, 1991

[54] LEVO-CIPROFIBRATE

[75] Inventors: Eugene H. Cordes, Town of Radnor, Pa.; George J. Ellames, Alnwick, England; John M. Herbert, Alnwick, England; David I. Smith, Alnwick, England

[73] Assignee: Sterling Drug Inc., New York, N.Y.

[21] Appl. No.: 522,607

[22] Filed: May 11, 1990

[51] Int. Cl.$^5$ ............................................. C07C 59/54
[52] U.S. Cl. ..................................................... 562/469
[58] Field of Search ......................................... 562/469

[56] References Cited

U.S. PATENT DOCUMENTS 3,948,973 4/1976 Phillips ................................ 562/469

Primary Examiner—Paul J. Killos
Attorney, Agent, or Firm—Theodore C. Miller; Paul E. Dupont

[57] ABSTRACT

Levo-ciprofibrate or a pharmaceutically acceptable salt thereof is disclosed.

5 Claims, No Drawings

LEVO-CIPROFIBRATE

BACKGROUND OF THE INVENTION

Field of the Invention

The invention relates to levo-ciprofibrate, which is useful as a serum lipid lowering agent, and method of use and compositions thereof.

SUMMARY OF THE INVENTION

In a first composition of matter aspect the invention is levo-ciprofibrate, which is (1)-(−)-2[4-(2,2-dichlorocyclopropyl)phenoxy]-2-methylpropanoic acid, or a pharmaceutically acceptable salt thereof.

In a process aspect the invention is the method of reducing the concentration of serum lipids in a mammal comprising administering to the mammal an effective serum lipid lowering amount of levo-ciprofibrate or a pharmaceutically acceptable salt thereof.

In a second composition of matter aspect the invention is a composition which comprises an effective serum lipid lowering concentration of levo-ciprofibrate or a pharmaceutically acceptable salt thereof and a pharmaceutically acceptable vehicle.

DETAILED DESCRIPTION OF THE INVENTION INCLUSIVE OF THE PREFERRED EMBODIMENTS

Preparation of Levo-ciprofibrate

In a first method of preparation levo-ciprofibrate is prepared by resolving racemic ciprofibrate by fractional crystallization of a salt thereof with an optically active amine. The preferred optically active amine is (S)(−)-α-methylbenzylamine. The preferred solvent is acetonitrile.

In a second method of preparation levo-ciprofibrate is prepared by first resolving 4-(2,2-dichlorocyclopropyl)aniline using (+)-tartaric acid and then synthesizing levo-ciprofibrate from the resulting (−)-4-(2,2-dichlorocylopropyl)aniline by the steps of diazotization-hydrolysis using sodium nitrite in aqueous sulfuric acid at 0°–10° C., then condensing the resulting (−)-4-(2,2-dichlorocyclopropyl)phenol with acetone and chloroform in aqueous alkali at 0°–100° C.

The following examples illustrate the method of preparation.

EXAMPLE 1

(1)-(−)-2-(4-(2,2-Dichlorocyclopropyl)phenoxy)-2-methylpropionic acid

A solution of (R)-(+)-α-methylbenzylamine (28.5 ml) in acetonitrile (50 ml) was added to a solution of 2-(4-(2,2-dichlorocyclopropyl)phenoxy)-2-methylpropionic acid (1) (128.15 g) in acetonitrile (1.45 L) at room temperature and left standing for 3 hours. The resulting crystals of the salt of (R)-(+)-α-methylbenzylamine with (1), A (23.9 g), were removed by filtration. The filtrate was concentrated by evaporation under reduced pressure and a second crop of the salt, B (12.0 g), removed by filtration. A third crop, C (28.6 g), was obtained similarly and the residual filtrate was evaporated to dryness under reduced pressure to yield a gum D.

The crystalline material C was suspended in dilute hydrochloric acid (200 ml, 2M) and extracted three times with diethyl ether. The combined organic phases were washed consecutively with distilled water and brine before being dried over anhydrous magnesium sulphate. The organic phase was then removed under reduced pressure to afford a white solid (22.89 g) with $[\alpha]_D^{21}$ (EtOH) of −7.92°.

The samples A, B and D were extracted similarly to afford white solids with mass and $[\alpha]_D^{21}$ (EtOH) respectively; (15.81 g) $[\alpha]_D^{21}$ +32.07°, (8.34 g) $[\alpha]_D^{21}$ +25.16° and (70.50 g) $[\alpha]_D^{21}$ −9.03°.

The white solids resulting from the above hydrolyses of salt samples C and D were combined and dissolved in acetonitrile (975 ml). To this solution was added a solution of (S)-(−)-α-methylbenzylamine (25 ml) in acetonitrile (75 ml) at room temperature. After 2 hours the crystalline salt of partially resolved (1) with (S)-(−)-α-methylbenzylamine (42.21 g) was removed by filtration. This material was suspended in dilute hydrochloric acid (350 ml, 2M) and extracted three times with diethyl ether. Combined organic phases were washed sequentially with water and brine before being dried over anhydrous magnesium sulphate. The organic phase was removed by evaporation under reduced pressure to afford a white solid (27.69 g) with $[\alpha]_D^{21}$ (EtOH) of −31.02°.

The above salt formation between partially resolved (1) and (S)-(−)-α-methylbenzylamine and subsequent hydrolysis was repeated a further seven times until material (514 mg) with $[\alpha]_D^{21}$ of −67.11° was obtained. This material (400 mg) was combined with a similarly derived sample (440 mg) of $[\alpha]_D^{21}$ of −67.83° and dissolved in diethyl ether (50 ml). This solution was dried over anhydrous magnesium sulphate and the organic phase removed by evaporation under reduced pressure to afford, as an amorphous white solid, (1)-(−)-2-(4-(2,2-dichlorocyclopropyl)phenoxy)-2-methylpropionic acid (737 mg), m.pt. 71.6°–75.2° C., (Found: C, 53.94; H, 4.91%:$C_{13}H_{14}Cl_2O_3$ requires C, 54.00: H, 4.88%).

(d)-(+)-2-(4-(2,2-Dichlorocyclopropyl)phenoxy)-2-methylpropionic acid

The white solids resulting from the above hydrolyses of salt samples A and B were combined and salt formation between partially resolved (1) and (R)-(+)-α-methylbenzylamine and subsequent hydrolysis was repeated a further eight times until material (452 mg) with $[\alpha]_D^{21}$ of +64.31° was obtained. This was combined with a similarly derived sample (890 mg) with $[\alpha]_D^{21}$ of +62.71°. This combined sample was further crystalised as the salt with (R)-(+)-α-methylbenzylamine and subsequently hydrolysed to afford, as an amorphous white solid, (d)-(+)-2-(4-(2,2-dichlorocyclopropyl)phenoxy)-2-methylpropionic acid (630 mg), m.pt 71.6°–75.2° C., (Found: C, 54.05; 4.90%: $C_{13}H_{14}Cl_2O_3$ requires C, 54.00:H, 4.88%) with $[\alpha]_D^{21}$ (EtOH) of +66.70°.

The enantiomeric purity of the above samples was measured by analytical high performance liquid chromatography (hplc) of the corresponding methyl esters on a Chiracel OA column eluted with methanol/water (21:19). The methyl esters were prepared as exemplified below.

(1)-(−)-2-(4-(2,2-Dichlorocyclopropyl)phenoxy)-2-methylpropionic acid methyl ester (1)-(−)-2-(4-(2,2-Dichlorocyclopropyl)phenoxy)-2-methylpropionic acid (30 mg) in methanol (4.5 ml) and concentrated sulphuric acid (2 drops) were heated under reflux for 1.5 hours. The solution was concentrated by evaporation under reduced pressure and the residue dissolved in diethyl ether (10 ml), washed twice with saturated aqueous sodium hydrogen carbonate, water and brine, before being dried over anhydrous magnesium sulphate. The organic phase was removed by evaporation under reduced pressure to afford the desired (1)-(−)-2-(4-(2,2-dichlorocyclopropyl)phenoxy)-2-methylpropionic acid methyl ester as a white solid (22 mg).

Under the hplc conditions described above, the (1)-(−)-2-(4-(2,2-dichlorocyclopropyl)phenoxy)-2-methylpropionic acid methyl ester was analysed as having an excess of the desired enantiomer over the racemate of 95.5%. The analogously prepared (d)-(+)-2-(4-(2,2-dichlorocyclopropyl) phenoxy)-2-methylpropionic acid methyl ester was analysed by the same method as having an excess of the desired enantiomer over the racemate of 94.0%.

EXAMPLE 2

Synthesis of
(−)-2[4-(2,2-Dichlorocyclopropyl)phenoxy]-2-methylpropanoic acid 4-(2,2-Dichlorocyclopropyl)aniline A solution of (+)-tartaric acid (33.3 g, 0.22 mol) in methanol (1 L), was added to a solution of 4-(2,2-dichlorocyclopropyl)aniline (90 g, 0.44 mol) in methanol (1 L) and warmed to 50° C. The solution was allowed to cool to room temperature overnight. The resulting crystals were removed by filtration and added to an aqueous solution of sodium hydroxide (1M, 1 L) before being extracted with diethyl ether (3×200 ml). The combined organic phases were washed with distilled water before being dried over anhydrous magnesium sulphate. The solvent was then removed by evaporation under reduced pressure to afford partially resolved (−)-4-(2,2-dichlorocyclopropyl)aniline (23.7 g) with an $[\alpha]_D^{21}$ (EtOH) of −96°.

The above was repeated with further batches of 4-(2,2-dichlorocyclopropyl)aniline until a quantity (142.4 g, 0.70 mol) of partially resolved material was accumulated. This material was dissolved in methanol (1.57 L) and added to a solution of (+)-tartaric acid (97.7 g, 0.65 mol) in methanol (1.57 L). The solution was allowed to stand overnight at room temperature. The resulting crystals were removed by filtration and added to an aqueous solution of sodium hydroxide (1M, 1.5 L) before being extracted with diethyl ether (4×200 ml). The combined ethereal extracts were washed with water, and then brine, before being dried over anhydrous magnesium sulphate. The organic phase was removed by evaporation under reduced pressure to afford resolved (−)-4-(2,2-dichlorocyclopropyl)aniline with an $[\alpha]_D^{21}$ (EtOH) of −104°.

A sample of this material was analysed by high performance liquid chromatography on a ChiralCel column (CA-1) in ethanol:water (7:3) as mobile phase, and determined to have an enantiomeric ratio of 95:5 in favour of the (−)-enantiomer.

(−)-4-(2,2-Dichlorocyclopropyl)phenol (−)-4-(2,2-Dichlorocyclopropyl)aniline (5 g, 0.024 mol) from the above resolution was dissolved in concentrated sulphuric acid (25 ml) and added in aliquots (1 ml) to iced water (100 ml). The mixture was allowed to stand overnight and the resulting precipitate then removed by filtration. The solid was suspended with stirring in sulphuric acid (0.05M, 70 ml) whilst being cooled to below 5° C. and a solution of sodium nitrite (2.2 g, 0.032 mol) in sulphuric acid (0.05M, 30 ml) added. After stirring for 1.5 hours the remaining precipitate was dissolved by addition of concentrated sulphuric acid (2.4 ml) and stirring maintained for a further 1.5 hours. The pH of the solution was then adjusted to 2 by addition of an aqueous solution of sodium hydroxide (10M) before being added to a stirred mixture of cupric nitrate hemipentahydrate (50 g, 0.21 mol) and sodium ascorbate (2.3 g, 0.012 mol) in distilled water (440 ml) and diethyl ether (150 ml). The mixture was stirred for 10 minutes before the organic phase was removed and the aqueous phase extracted with diethyl ether (3×100 ml). The combined organic phases were washed with distilled water, dried over anhydrous magnesium sulphate and the solvent removed by evaporation under reduced pressure to afford the crude (−)-4-(2,2-dichlorocyclopropyl)phenol (4.6 g) which was used directly in the following reaction.

(−)-2-[4-(2,2-Dichlorocyclopropyl)phenoxy]-2-methylpropanoic acid

The crude (−)-4-(2,2-dichlorocyclopropyl)phenol (4.6 g) from the previous reaction was dissolved in acetone (63.2 ml) and added slowly to a solution of sodium hydroxide (6.7 g, 0.17 mol) in acetone (42 ml) under reflux. After 15 minutes, chloroform (1.5 g, 0.013 mol) in acetone (25 ml) was added at a rate which maintained a gentle reflux. After one hour, the solvent was removed by evaporation under reduced pressure and the resulting solid partitioned between distilled water (350 ml) and diethyl ether (100 ml). The organic phase was removed and the aqueous phase acidified with dilute hydrochloric acid and extracted with diethyl ether (2×100 ml). The combined ethereal extracts were washed with water, dried with anhydrous magnesium sulphate and the solvent removed by evaporation under reduced pressure to afford the crude product (3.5 g). This material was chromatographed on silica gel eluting with diethyl ether/hexane/glacial acetic acid (4:15:1) to afford (−)-2-[4-(2,2-dichlorocyclopropyl)phenoxy]-2-methylpropanoic acid (0.5 g) with properties identical with that obtained by the described resolution of racemic material with (−)-α-methylbenzylamine.

A sample of this material was methylated and analysed by chiral HPLC, as described for the resolved material, and found to have an enantiomeric ratio of greater than 95:5 in favour of the (−)-enantiomer.

Synthesis of
(+)-2-[4-(2,2-Dichlorocyclopropyl)phenoxy]-2-methylpropanoic acid (+)-4-(2,2-Dichlorocyclopropyl)aniline 4-(2,2-Dichlorocyclopropyl)aniline (50 g, 0.25 mol), enriched with the (+)-enantiomer following partial resolution with (+)-tartaric acid as described above, was dissolved in methanol (500 ml) to which was added a solution of (−)-tartaric acid (22.7 g, 0.15 mol) in methanol (500 ml). The solution was allowed to stand overnight and the resulting crystals removed by filtration. These crystals were added to an aqueous solution of sodium hydroxide (1M, 350 ml) and the solution extracted with diethyl ether (3×100 ml). The combined ethereal extracts were dried over anhydrous magnesium sulphate and the solvent removed by evaporation under reduced pressure. The residue (18.1 g) was treated analogously a further two times until (+)-4-(2,2-dichlorocyclopropyl)aniline (7.8 g) was obtained with an $[\alpha]_D^{21}$ (EtOH) of +107°.

(+)-4-(2,2-Dichlorocyclopropyl)phenol (+)-4-(2,2-Dichlorocyclopropyl)aniline (3 g, 0.015 mol) from the previous resolution was dissolved in concentrated sulphuric acid (15 ml) to which was added iced water (30 ml). With the reaction temperature maintained below 5° C., a solution of sodium nitrite (1.3 g, 0.019 mol) in distilled water (15 ml) was added. After a further 5 minutes, urea (0.27 g, 0.0045 mol) was added to eliminate excess nitrous acid. The pH of the mixture was then adjusted to 3 by addition of an aqueous solution of sodium hydroxide (10M) whilst the temperature of less than 5° C. was maintained. This mixture was then added slowly to a vigorously stirred mixture of cupric nitrate hemipentahydrate (60 g, 0.26 mol) and sodium ascorbate (2.8 g, 0.014 mol) in distilled water (530 ml) and diethyl ether (200 ml). After 5 minutes the organic phase was removed and the aqueous phase extracted with diethyl ether (3×100 ml). The combined organic phases were washed with distilled water, dried over anhydrous magnesium sulphate and the solvent removed by evaporation under reduced pressure to afford crude (+)-4-(2,2-dichlorocyclopropyl)phenol (3.1 g) which was used directly in the following reaction.

(+)-2-[4-(2,2-Dichlorocyclopropyl)phenoxy]-2-methylpropanoic acid

The crude (+)-4-(2,2-dichlorocyclopropyl)phenol (3.1 g) from the previously reaction was dissolved in acetone (42 ml) and added slowly to a solution of sodium hydroxide (4.5 g, 0.11 mol) in acetone (27 ml) under gentle reflux. After 5 minutes, a solution of chloroform (1.0 g, 0.008 mol) in acetone (17 ml) was added at a rate so as to maintain this reflux. After one hour the solvent was removed by evaporation under reduced pressure and the resulting solid partitioned between distilled water (150 ml) and diethyl ether (3×50 ml). The aqueous phase was acidified with dilute hydrochloric acid and extracted with diethyl ether (3×50 ml). The combined organic phases were washed with distilled water, dried over anhydrous magnesium sulphate and the solvent removed by evaporation under reduced pressure. The resulting solid was chromatographed on silica gel eluting with diethyl ether/hexane/glacial acetic acid (4:15:1) and the product recrystallised from hexane to afford (+)-2-[4-(2,2-dichlorocyclopropyl)phenoxy]-2-methylpropanoic acid (460 mg) with properties identical to that obtained by resolution of racemic material with (+)-α-methylbenzylamine as described above.

A sample of this material was methylated and analysed by chiral HPLC, as described for the resolved material, and found to have an enantiomeric ratio of greater than 95:5 in favour of the (+)-enantiomer.

Biological Properties of Levo-ciprofibrate

Racemic ciprofibrate, which is described by U.S. Pat. No. 3,948,973 and whose disclosure is incorporated herein by reference and is an effective serum lipid lowering agent in humans, has a half-life of about 100 hr. in the rat. Levo-ciprofibrate has a half-life of 24 hr. in the rat. This difference will result in more rapid achievement of steady state serum concentration and more rapid onset of serum lipid lowering effect by levo-ciprofibrate than by racemic ciprofibrate. Moreover, by virtue of the shorter half-life, patients will be exposed for a shorter time to any possible adverse effect of levo-ciprofibrate. The daily dosage is from about 50 mg. to about 500 mg.

The Compositions

The compositions in accordance with the second composition of matter aspect of the invention can be prepared for oral, parenteral, rectal or vaginal administration and can be in solid or liquid dosage form including capsules, tablets, suppositories, solutions, suspensions and emulsions. Conventional pharmaceutically acceptable vehicles and techniques are used in preparing these dosage forms.

We claim:

1. (1)-(−)-2-[4-(2,2-Dichlorocyclopropyl)phenoxy]-2-methylpropionic acid or a pharmaceutically acceptable salt thereof.

2. The method of reducing the concentration of serum lipids in a mammal comprising administering to the mammal an effective serum lipid lowering amount of levo-ciprofibrate or a pharmaceutically acceptable salt thereof.

3. A composition which comprises an effective serum lipid lowering concentration of levo-ciprofibrate or a pharmaceutically acceptable salt thereof and a pharmaceutically acceptable vehicle.

4. The process of preparing a compound according to claim 1 comprising resolving racemic ciprofibrate by fractional crystallization of a salt thereof with an optically active amine.

5. The process of preparing a compound according to claim 1 comprising first resolving 4-(2,2-dichlorocyclopropyl)aniline using (+)-tartaric acid and then subjecting the resulting (−)-4-(2,3-dichlorocyclopropyl)aniline to diazotizationhydrolysis using sodium nitrite in aqueous sulfuric acid at 0°–10° C. and then condensing the resulting (−)-4-(2,2-dichlorocyclopropyl)phenol with acetone and chloroform in aqueous alkali at 0°–100° C.

* * * * *